(12) United States Patent
Hudson

(10) Patent No.: US 7,115,232 B2
(45) Date of Patent: Oct. 3, 2006

(54) FLUORESCENCE VALIDATION MICROPLATE AND METHOD OF USE

(76) Inventor: Gordon S. Hudson, 13 Willis Ct., Durham, NC (US) 27704

( * ) Notice: Subject to any disclaimer, the term of this patent is extended or adjusted under 35 U.S.C. 154(b) by 104 days.

(21) Appl. No.: 10/154,623

(22) Filed: May 24, 2002

(65) Prior Publication Data

US 2003/0012702 A1    Jan. 16, 2003

(51) Int. Cl.
| G01N 21/64 | (2006.01) |
| G01N 1/10 | (2006.01) |
| G12B 13/00 | (2006.01) |
| G01D 18/00 | (2006.01) |
| B01L 3/00 | (2006.01) |
| B01L 9/06 | (2006.01) |

(52) U.S. Cl. .................. 422/102; 24/227; 24/229; 24/230; 250/252.1; 356/243.1; 356/244; 356/246; 378/207; 422/82.07; 422/82.08; 422/99; 422/101

(58) Field of Classification Search ....... D24/226–227, D24/229–230; 250/252.1; 356/243.1, 244, 356/246; 378/207; 422/82.07–82.08, 85.07–85.08, 422/99–104; 435/968
See application file for complete search history.

(56) References Cited

U.S. PATENT DOCUMENTS

| 4,357,142 | A | * | 11/1982 | Schall et al. ............... 436/531 |
| 4,448,534 | A | * | 5/1984 | Wertz et al. ................. 356/435 |
| 4,730,922 | A | * | 3/1988 | Bach et al. ................... 356/73 |
| 4,892,405 | A | * | 1/1990 | Sorensen et al. .......... 356/243.8 |
| 5,061,639 | A | * | 10/1991 | Lung et al. .................. 436/164 |
| 5,157,455 | A | * | 10/1992 | Macri et al. .............. 356/243.8 |
| 5,183,761 | A | * | 2/1993 | Freeman et al. ................ 436/8 |
| 5,213,505 | A | * | 5/1993 | Laipply ........................ 434/96 |
| 5,225,680 | A | * | 7/1993 | Yrjonen et al. .............. 250/362 |
| 5,234,665 | A | * | 8/1993 | Ohta et al. ...................... 422/73 |
| 5,278,415 | A | * | 1/1994 | Yrjonen et al. .............. 250/362 |
| 5,324,635 | A | * | 6/1994 | Kawase et al. ............ 435/7.94 |
| 5,355,215 | A | * | 10/1994 | Schroeder et al. ........... 356/317 |
| 5,436,718 | A | * | 7/1995 | Fernandes et al. ............ 356/73 |
| 5,693,463 | A | * | 12/1997 | Edwards et al. ................ 435/6 |
| 5,721,435 | A | * | 2/1998 | Troll ....................... 250/559.29 |
| 6,051,191 | A | * | 4/2000 | Ireland ........................ 422/102 |
| 6,106,783 | A | * | 8/2000 | Gamble ....................... 422/102 |
| 6,171,780 | B1 | * | 1/2001 | Pham et al. ..................... 435/4 |
| 6,187,267 | B1 | * | 2/2001 | Taylor et al. .................. 422/52 |
| 6,264,891 | B1 | * | 7/2001 | Heyneker et al. ............. 422/64 |
| 6,348,965 | B1 | * | 2/2002 | Palladino et al. ......... 356/243.1 |
| 6,471,916 | B1 | * | 10/2002 | Noblett .................... 422/82.08 |

FOREIGN PATENT DOCUMENTS

WO    WO 9845406 A1 * 10/1998

* cited by examiner

Primary Examiner—Arlen Soderquist
(74) Attorney, Agent, or Firm—Passé Intellectual Property; James Passé

(57) ABSTRACT

A fluorescence validation microplate for testing the validity of a fluorometer is provided which can efficiently and cost-effectively test fluorometers to determine linearity, alignment, reproducibility, filter integrity, and cross-talk, each of which is important to proper functioning of the fluorometer.

9 Claims, 5 Drawing Sheets

FLUORESCENCE VALIDATION MICROPLATE AND METHOD OF USE

BACKGROUND OF THE INVENTION

1. Field of the Invention

The present invention relates to the measurement of fluorescence by a fluorescence microplate reader. In particular, the present invention relates to a fluorescence validation microplate which is used to validate the reliability of the information received from a fluorescent assay microplate during its reading in a fluorescence microplate reader.

2. Description of Related Art

The growth of biological research and new pharmaceutical compound screening and in some cases, medical diagnostics has created a need for handling large numbers of test samples at one time in order to control costs and efficiently handle these large numbers of samples. A number of analytical methods are now available for high throughput screening of these samples. One of the fastest growing screening methodologies in life science is fluorescence spectroscopy. With this method, the fluorescent emission of test samples tagged with a fluorescent material or with intrinsic fluorescence are measured. Fluorescent emission measurement techniques rival, at this time, those of radioactive assay without the inherent danger of radioactive probes. Typically, large numbers of samples are processed for fluorescence emission reading by placement in a multi-well sample plate called a microplate. These microplates are typically a rectangular array of wells, usually 24 or 96 wells in typical examples, but even 384 well and 1536 well microplates are used. Typically, each well in a 96 well microplate is approximately 0.3–0.4 ml. Plates with larger numbers of wells have even smaller volumes. These microplate wells are filled with test samples and then placed in a special detector system called a fluorescence microplate reader (also called a fluorometer) for measuring the relative fluorescence emissions (normally as RFU's or relative fluorescence units).

Although fluorescence microplates and fluorometers are of great utility in automated screening, there are a number of issues connected with their use that affect the reliability of their use. A fluorometer has a series of optical devices wherein each device is positioned to correspond to a well in a microplate holding test samples. In the alternative, the fluorometer is fitted with a single optical device and either the plate, the reading device, or both is moved to the appropriate reading position. Use of the microplate on the fluorometer must involve alignment of each sample well with the optical device on the fluorometer. Alignment is typically done by physically moving either the microplate, the fluorometer optical device(s) or both. Movement of microplates or optical devices is done using stepper motors wherein the movement is guided on a certain number of (factory calibrated) steps from a "home" position. Alignment is adversely affected when one or more of the aligned components involved is shifted in position or becomes damaged. If, for any reason, the alignment is incorrect, the wells will not be centered properly, resulting in incorrect fluorescence measurements.

The optics used to measure fluorescence must avoid detecting transmission of fluorescence from one sample well as fluorescence from an adjacent well. This adjacent well detection problem is called "cross-talk". Cross-talk is extremely undesirable because it means the photon emissions detected, by a particular optical device at a given location originated from the sample in a different well. In a worse case scenario, a particular well optical device is detecting fluorescent cross-talk from all the surrounding or adjacent wells. This can be as many as eight wells in a standard microplate set-up. In a minimum problem scenario, cross-talk only occurs from an adjacent (single) well but is still obviously undesirable.

Linearity of the sample readings is also extremely important to control. Linearity is a measure of the relationship between different amounts of fluorescence emissions in a series of wells as measured by their RFU's. A linear dose response relationship should exist between the measured RFU's and the strength of the fluorescence emissions. Linearity is an indication of the relative concentration of fluorescence emissions in the series of wells. As the optical, electronic and other components of the fluorometer age, the detection efficiency can be diminished at different RFU's and the linearity is affected especially at high and low fluorescence intensities. To a certain extent, these problems have been addressed by software programs and by advancing technologies with the readers themselves. However, these solutions do not solve all the linearity problems with fluorometers.

Another problem with the fluorometers is the necessity to select discrete wavelengths of both the excitation and emission light to measure fluorescence. This is done using interference filters, diffraction gratings, acousto-optical tunable filters or a variety of other devices. These devices are notoriously fragile, subject to damage by water, scratches, oxidation and the like causing fluorometers to give inaccurate results.

It would be useful therefore if there were a device capable of providing necessary information, input or feedback to detect, help correct or eliminate these problems for fluorometers. Specifically, what is needed and has not previously been provided by the art is a method or device for testing the validation of results obtained with a fluorometer.

SUMMARY OF THE INVENTION

The present invention relates to a fluorescence validation microplate for testing the validity of a fluorometer comprising one or more of the following:
 (a) a set of measurement positions establishing a cross-talk one-in-eight well design test;
 (b) a set of measurement positions establishing a cross-talk eight-around-one well design test;
 (c) a plurality of wells establishing a linearity test;
 (d) a plurality of wells comprising at least a first and second fluorophore; and
 (e) a set of wells establishing an alignment test.

In accordance with the present invention and objectives, a novel fluorescence validation microplate (called a validity plate hereinafter) is disclosed. The validity plate of the invention is a microplate where the construction is such that the reliability of a fluorometer may be tested therefrom. The validity plate is not designed to house test samples; rather, it is designed to be fitted with fluorophores which enables a fluorometer operator to test the accurate functioning of a fluorometer. The validity plate contains measurement positions corresponding to a standard microplate and accordingly to the measurement positions on the corresponding fluorometer. The measurement positions on the validity plate comprise either a well fitted with a fluorophore or a blank position or a well not fitted with a fluorophore.

A fluorophore fitted in a well of validity plate of the invention can be any solid fluorescent material of known excitation and emission wavelengths. The excitation and emission wavelengths should be within the range of those measured by corresponding fluorometers. Typical fluorometers excite test samples in the wavelength range of 200–900 nm and measure emission in the range of 280–950 nm. The fluorophores can be organic or inorganic and can be on a film, embedded in a polymer matrix, coated or frosted onto a rigid slide, or in any physical solid form with consistent and stable fluorescent intensity. So, for example, an embodiment of the invention may use standard fluorescent plastic sheets of Atoglas, from Atofina Chemicals, cut to fit the appropriate trenches provided in the validity plate. At least three colors are currently available from Atofina, blue (#3192), green (#3190), and red (#3152). Fluorescent papers, coatings or the like could also be used. Fluorophores are shaped to be placed either in a well or at the bottom of a well in a position to be read by a fluorometer making a measurement of a well. For clarity, such placement herein shall be referred to as having been "fitted".

The entrance of any of the wells of the invention can also, in a preferred embodiment, be countersunk i.e. beveled. In a countersunk well, the well starts below the surface of the plate due to widening of the well at the surface as would be done to countersink the head of a screw. This design has at least two benefits. First, because the optics of many fluorometers are oriented at an angle, it has been discovered that the beveled edges are necessary to allow light to reach the bottom of the wells where a fluorophore is typically located. Second, it has been found that the beveled edges can be cut to minimize reflection. While black anodized aluminum can be used to manufacture a validity plate in order to reduce reflection, some small amount of the excitation light may nevertheless still bounce off the black surface into the detector, slightly raising the background. The countersinking then tends to disperse the light which bounces off the surface of the validity plate.

The validity plate of the invention, preferably, should be constructed of an essentially rigid and durable material and which is preferably both light opaque and fluorescence opaque. Such opacity has been found to be critical when testing for cross-talk. The validity plate is also preferably constructed of a substantially non-reflective surface material and preferably of black or other very dark color. Embodiments of such preferred material include, aluminum, anodized aluminum, delrin, Kevlar, nylon, or polypropylene. In one embodiment, the validity plate consists of an upper plate and a lower plate held together in register via an attachment means such as fastening bolts. In another embodiment, the validity plate is constructed of a single piece plate with the fluorescent material fixed to the plate with adhesive, fasteners, or by other means. The validity plate of the invention is constructed essentially the same size as a microplate that would be used in the fluorometer being tested. The validity plate also has measurement positions corresponding to each of the optical devices or optical measurement positions in the fluorometer. For example, a 96-position fluorometer, the current standard size, the validity plate has 96 measurement positions.

A first test provided for by the validity plate of the invention is a test for cross-talk. The construction which enables this test to be carried out comprises two separate sets of measurement positions on the validity plate. A first set of measurement positions establish a one-in-eight well design test, and consists of a block of measurement positions corresponding to a 3 by 3 grid or 9 optical measurement positions on the fluorometer. The single center position consists of a fluorophore in a center well, while the outer eight positions have no fluorophore. The outer eight positions could be wells not fitted with a fluorophore or blank measurement positions with no wells. The one-in-eight design test enables the operator to test if a single well is cross-talking with one of its neighbor positions. In an ideal situation, the outer eight positions would read zero (after adjustment for background). Any reading above the background at any other position would indicate cross-talk. The validity plate also enables background to be determined by reading at a different measurement position with no fluorophore and not adjacent to wells with the same flourophore.

The second test provided for by the validity plate of the invention is also for testing for cross-talk. A second set of measurement positions establishes an eight-around-one design test and consists of the same 3 by 3 grid of measurement positions again corresponding to 9 optical measurement positions in the fluorometer. This time however, the validity plate construction provides for the exterior 8 positions to consist of a well fitted with a fluorophore and the center position with no fluorophore. This set of measurement positions tests for the "worse" case cross-talk situation where the center measurement position, which should have a zero optical reading when adjusted for background, will have some reading above that level if there is cross-talk from any or all of the surrounding measurement positions. Again, background can be determined as above.

The next test provided for by the construction of the validity plate of the invention relates to measuring the linearity of the fluorescence emission data read on a fluorometer. To test for linearity, a plurality of wells, each well containing a varying fluorescent emission are provided for the validity plate. In a first embodiment, each well is fitted with a different concentration of fluorophore. In another embodiment, a plurality of wells of decreasing diameter are placed on the validity plate at measurement positions corresponding to optical devices on the fluorometer each fitted with a fluorophore of the same emission intensity. In yet another embodiment provided for by the validity plate construction, identical wells, and fluorophores of the same emission intensity are used and the strength of emissions for each well varied by placing a filter of different strength in each well over the fluorophore.

Since each well in the linearity test discussed above produces a different fluorescent emission, the result of the readings on the fluorometer will produce a linear dose response curve, only if the fluorometer is operating correctly. So for example, in one embodiment of the validity plate using 7 wells, the first well (which are in many microplates actually 0.355 inch in diameter) would represent a relative emission value of 4 the second well a value of 3, the third, a value of 2, the fourth, a value of 1.2, the fifth, a value of 0.75, the sixth, a value of 0.5, and the seventh well, a value of 0.25. Valid readings produce, when plotted, a standard dose response curve (a straight line) while an error in reading shows up as a deviation in the otherwise smooth linear curve. While 7 wells produces a readable curve, more or less wells will work as well, depending on the size of the validity plate, other tests provided on the validity plate and the dynamic range of RFU to be tested. The average of several emission values in the linearity test measured by the fluorometer is preferably taken, for example, by placing multiple copies of the linearity test on the validity plate. The average of the measured values for each set of replicates is plotted against those in a previously validated reader. The so-called "$R^2$" value of a linear regression calculation must be higher than a pre-determined threshold of the reader tested to be accepted.

A fourth test provided for by the construction on the validity plate of the invention is one that tests for proper alignment of the microplate relative to the optical reading positions on the fluorometer as a measure of the alignment of the fluorometer. For this purpose, a set of wells at or near at least two edges of the microplate are each fitted with the same exact amount of fluorophore. In one embodiment, the two edges are opposite edges of the microplate (i.e. left and right or top and bottom). Deviation of the fluorescence readings of this set of wells can be attributed to alignment problems. In one embodiment, these wells are smaller than normal size well diameter, e.g. ½ standard diameter, and are positioned on opposing sides of the validity microplate, for example, in the first and last column of the microplate. In one embodiment, the entire first and last column would be wells designed to test alignment. In another embodiment, the wells are twice as deep as normal wells. Each of the wells are constructed to tight tolerances. Narrower wells and deeper wells make proper reading of the well more difficult and cause misalignment to show up easier. A properly aligned fluorometer will give essentially identical readings for each well within standard error. Misalignment will cause values to be skewed in such a manner that the misalignment can be determined. One method of evaluating the information is to calculate the slope of the values measured in column 1 and column 2 and another method is to compare the averages of column 1 to that of column 2. In another embodiment, a well in each of the four corners of the validity plate is used for alignment measurement.

The fluorometer can further be checked by a validity plate of the invention by providing the validity plate with two or more different fluorophores to check the filter integrity of the fluorometer. One or more wells of each fluorophore sample can be provided.

Another test possible with the validity plate is reproducibility verification. This is done by measuring the validity plate multiple times with the fluorometer to be evaluated and performing a standard statistical evaluation of the results expected with the fluorophore.

DESCRIPTION OF EMBODIMENTS OF THE INVENTION

Figure 1:
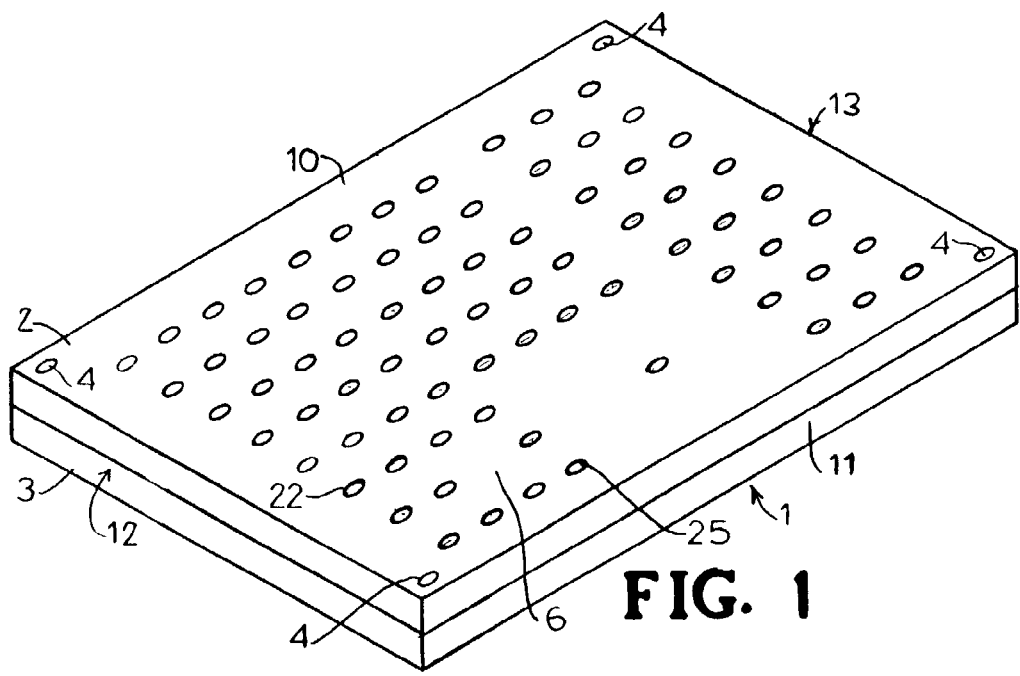
FIG. 1 is a perspective view of an embodiment of the present invention depicting a fluorescence validation microplate of the invention.

Referring to the figures, FIG. 1 is a perspective view of an embodiment of the present invention. The validity plate 1, depicted is one for testing a standard 96 position fluorometer. It consists of a top plate 2 and bottom plate 3 connected in alignment with bolts 4. The top 10 of the validity plate 1 and bottom 11 are indicated as well, as left side 12 and right side 13 of validity plate 1 for orientation are indicated.

The validity plate 1 has wells 25, 22 which are of varying diameters and/or depths and are arranged such that a variety of test can be performed. Each well shown is fitted with a fluorophore. The validity plate 1 also has blanks 6 which are solid measurement positions on the validity plate 1 with no well (and thus no fluorophore). Each well 22, 25 and blank 6 corresponds to an optical reading device measurement position on the fluorometer. In an embodiment not shown, the blanks are simply empty wells with no fluorophore.

Figure 2:
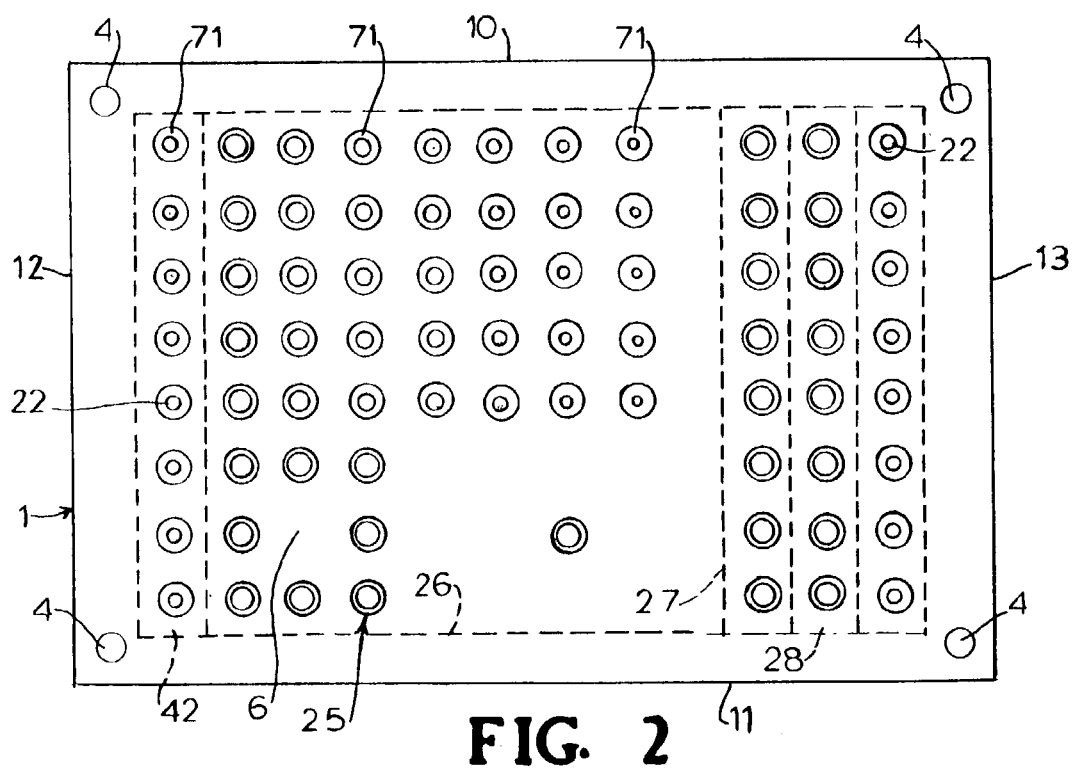
FIG. 2 is a top view of the embodiment of FIG. 1.

FIG. 2 is a top view of the embodiment of the invention of FIG. 1. Shown is the validity plate 1 with only the top plate 2 visible. Bolts 4 are also visible in the perspective. Fluorophore 42, 26, 27, 28 are shown below the surface of the top plate 2, each being of a different color fluorophore e.g. fluorescent red, blue or green, respectively. Wells 22 and 25 are thus fitted with a fluorophore 42, 26, 27, 28. Top 10, bottom 11, sides 12 and 13 are also depicted for orientation. Also depicted in this embodiment is countersunk edges 71.

Figure 3:
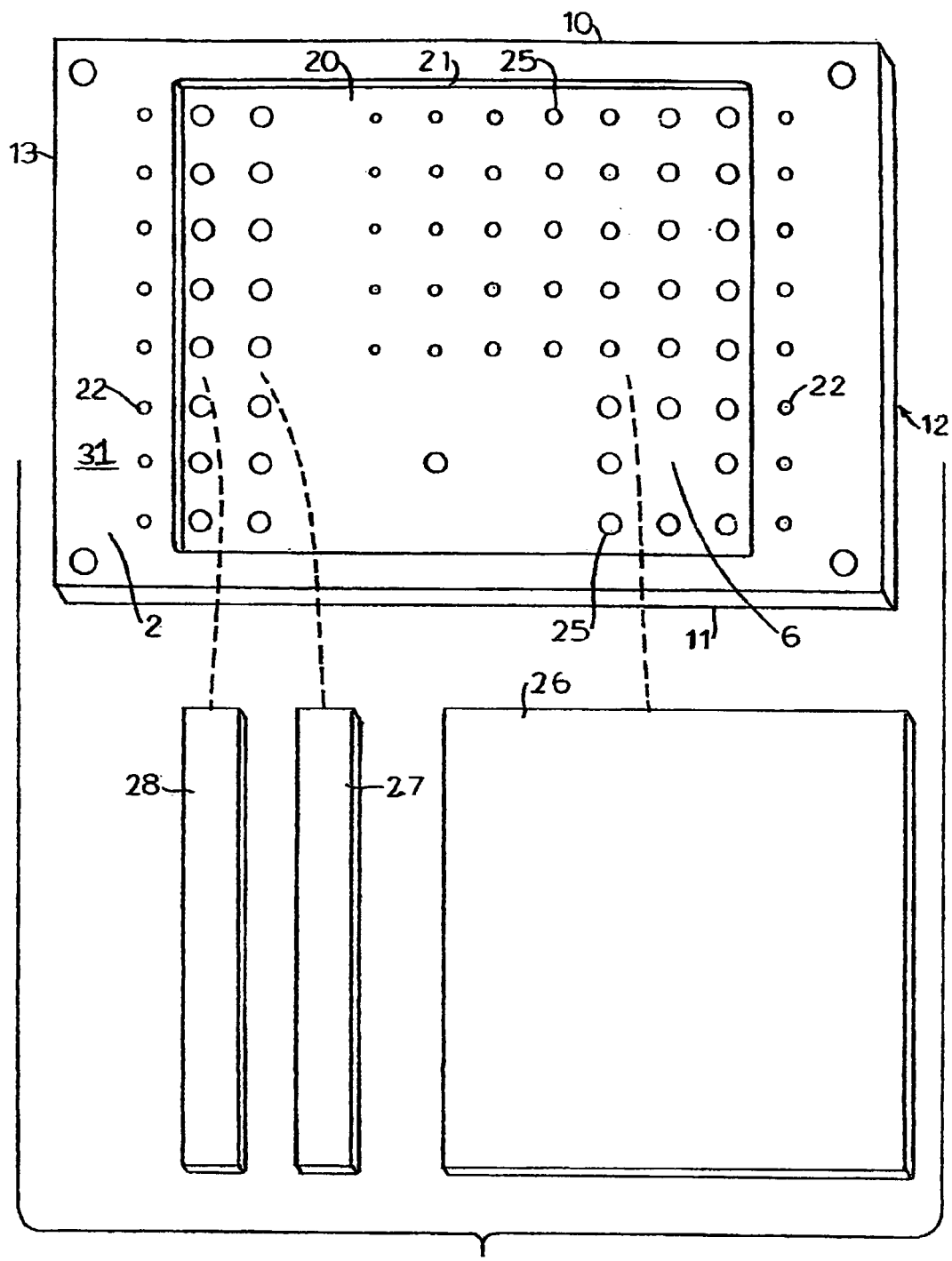
FIG. 3 is a view of the bottom surface of the top plate of the validity plate in position to receive the illustrated fluorophore of the invention in FIGS. 1 and 2.

FIG. 3 depicts a bottom view of the top plate 2 of a validity plate 1 of the invention which has been separated from the bottom plate 3 shown in FIG. 1. The fluorophores 26, 27, 28 are also shown in position to be fitted to the top plate 2, wells 22 on the ends of the plate as depicted extending all the way through the top plate 2. FIG. 3 also indicates that the center section of top plate 2 has been hollowed out to create trough 20 of thickness 21 which is approximately half the thickness of top plate 2. Accordingly, wells 25, in the trough 20 are only half the depth of the wells 22 not in trough 20.

In the embodiment shown in FIG. 3, trough 20 is fitted with fluorophores 26, 27 and 28 each by the same or different fluorophore as desired. Each fluorophore 26, 27 and 28 consist of a plastic fluorescent material the thickness of the trough 20 so that when placed in the trough 20, the fluorophores 26, 27 and 28 fit flush with the face 31 of the bottom of top plate 2 (see also FIG. 9 cross section). All wells 25 that are over trough 20 have a fluorophore fitted for reading by a fluorometer. Top 10, bottom 11, left side 12, and right side 13 are again shown in FIG. 3 for orientation purposes.

Figure 4:
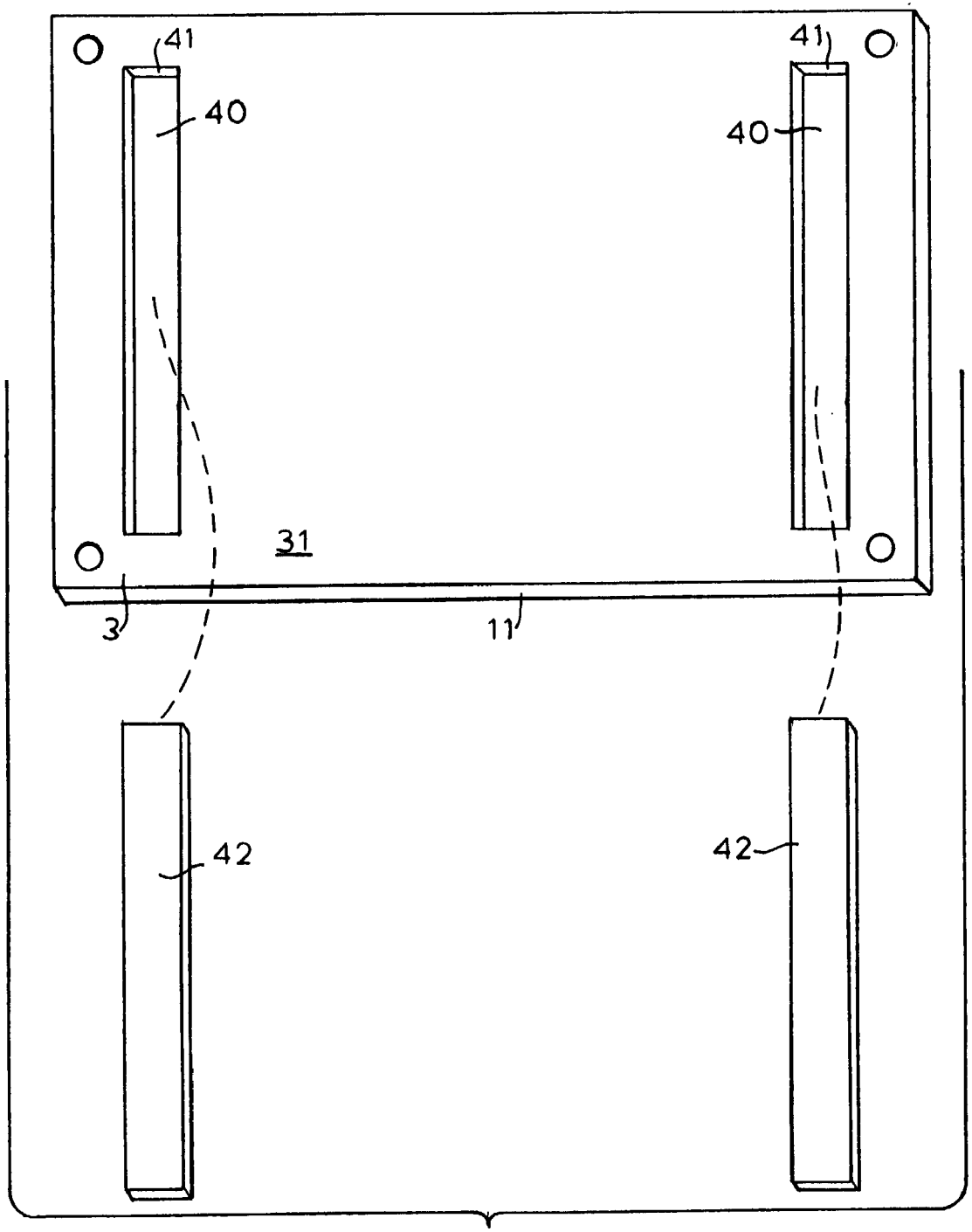
FIG. 4 is a top view of the bottom plate of the validity plate of the invention in position to receive the illustrated fluorophore.

FIG. 4 is an exploded view of the top 31 of the bottom plate 3 of the validity plate 1 of FIG. 1. None of the wells 25 and 22 extend into the bottom plate. Bottom plate 3, which is roughly the same thickness as top plate 2, has two troughs 40 of depth 41 approximately half of the thickness of the bottom plate 3. Fluorophores 42 similar to fluorescent material 26, 27 and/or 28 of FIG. 3, is fitted in the trough 41. These fluorophores 42 are fitted to the wells 22 shown in FIG. 3 which extend all the way through the top plate 2 of the microplate to provide fluorophore to wells 22.

Figure 5:
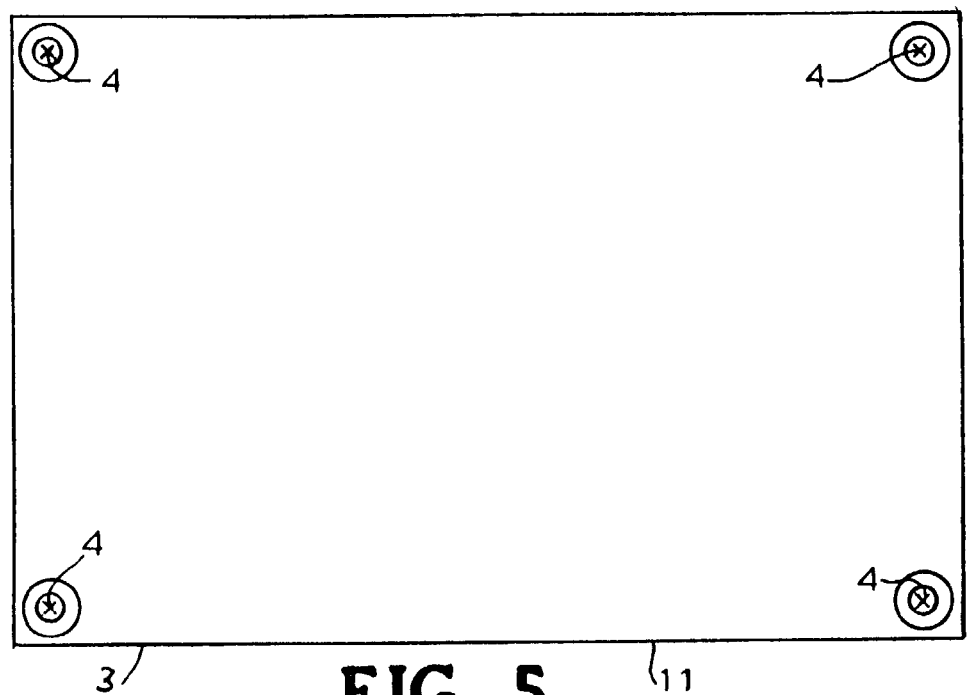
FIG. 5 is a bottom view of the bottom plate of the validity plate of the invention.

FIG. 5 is a bottom view of the bottom plate 3 of the validity plate 1 of the invention. It is solid except for bolts 4 for connecting bottom plate 3 to the top plate 2 of FIG. 3.

Figure 6:
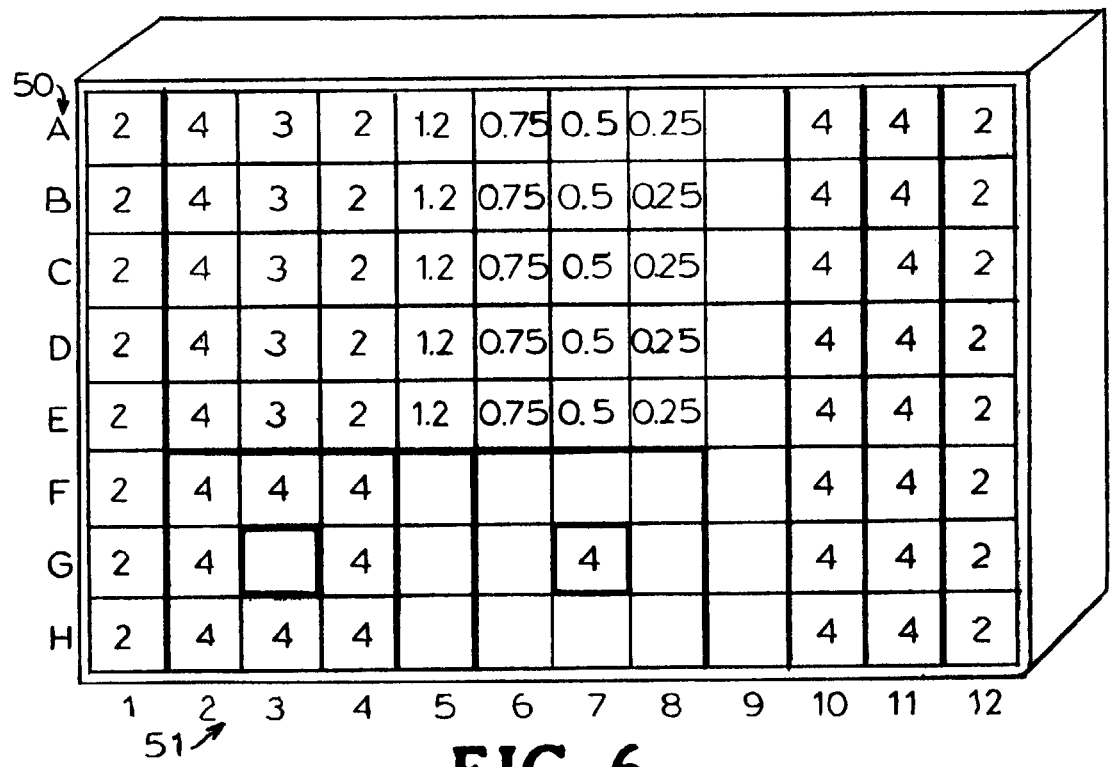
FIG. 6 is a schematic, showing of the relative size of the validity plate wells in the configuration of the positions in FIG. 1.

FIG. 6 is a schematic view illustrating the relative inner diameter of the wells and the relative location of the measurement positions of the embodiment of the invention depicted in FIG. 1. Horizontal rows are indicated by letters, A through H numbered 50 and vertical columns are indicated by numbers 1 through 12 numbered 51. A standard fluorescent microplate well inner diameter was picked to use on a validity plate and assigned a relative value of 4. Other numbers are then relative to the diameter size of this well. Where there is no number, there is a measurement position with no well or in the alternative, no fluorophore.

Columns 1 and 12 correspond to columns where each well is ½ the standard diameter (and as indicated above twice the depth). These wells correspond to those wells used for testing alignment. The wells consisting of rows A–E in columns 2–8 are wells of decreasing diameter and represent the set of wells for the linearity test of the invention. Columns 10 and 11 are wells fitted with different fluorophores. The set of measurement positions consisting of wells and blanks establishing the cross-talk test is indicated by rows F–H in columns 2–4 and 6–8 which represent the one-in-eight and eight-around-one test respectively. In this embodiment, column 9 are blanks. These measurement positions can be used to test for background.

Figure 7:
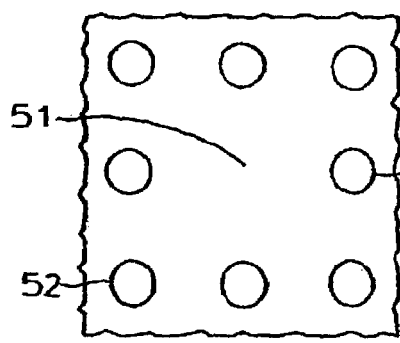
FIG. 7 is an enlarged fragmentary view of a portion of the validity plate of the invention provided with an 8-around-1 design test.

FIG. 7 depicts a fragmentary view of a portion of a validity plate depicting a set of reading positions on the validity plate establishing an eight-around-one design test. Eight-around-one center 51 is a measurement position with no fluorophore. Eight-around-one 8 outer wells 52 are wells that are fitted with a fluorophore. In using this design on a validity plate, eight-around-one center 51 should be read by a fluorometer and have essentially a zero value adjusting for background. Any value at that position over background would be due to cross-talk from one or more of the eight-around-one outer wells 52.

Figure 8:
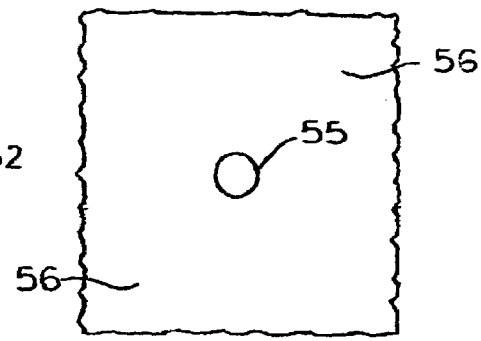
FIG. 8 is an enlarged fragmentary view of a portion of the validity plate of the invention providing for a 1-in-8 design test.

FIG. 8 is a fragmentary view of a portion of a validity plate of the invention depicting a set of measurement positions on a validity plate establishing a one-in-eight design test. In this view, one-in-eight center 55 is a well fitted with a fluorophore. One-in-eight center 55 is surrounded by eight, one-in-eight outer positions 56 which measurement positions are either blank positions or wells with no fluorophore. This test measures emissions at each of the one-in-eight positions. Any emissions measured at any of the one-in-eight outer positions 56 when adjusted for background would indicate cross-talk from the one-in-eight center positions 55.

Figure 9:
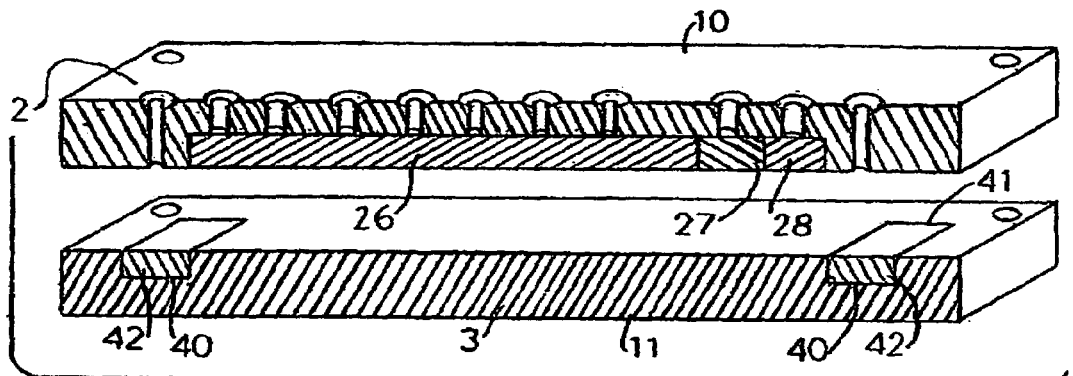
FIG. 9 is a fragmentary perspective, cross section view of a portion of the top and bottom plates of a validity plate of the invention.

FIG. 9 is a fragmentary prospective, exploded cross sectional view of a portion 15 of the top and bottom plates of a validity plate of the invention as depicted in FIG. 1. Shown is upper plate 2 and lower plate 3. As can be seen in this perspective, fluorophores 42 are used in the alignment test, fluorophore 26 is for use in the one-in-eight, eight-around-one and linearity tests and alternate fluorophores 27, 28.

Figure 10:
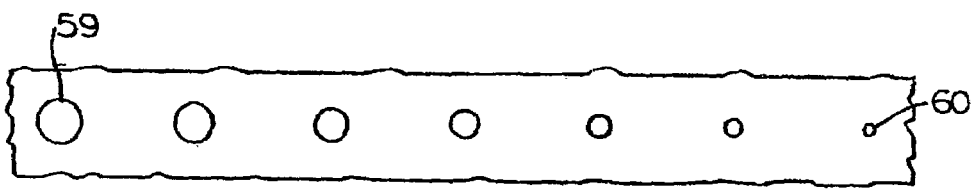
FIG. 10 is an enlarged fragmentary view and depicts a series of decreasing diameter wells in an embodiment of the invention establishing a linearity test area on the validity plate.

FIG. 10 is an enlarged fragmentary view of a portion of the validity plate of the invention depicting the measurement positions sued for a linearity test of the invention. In this aspect of the invention, each well is outfitted with a fluorophore and the diameter of the well varies in size from largest linearity well 59 to smallest linearity well 60. Each well in between is sized at a known diameter for example as depicted in FIG. 6.

Figure 11:
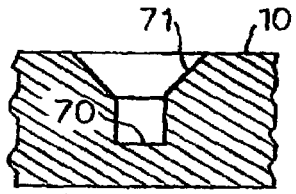
FIG. 11 depicts an enlarged fragmentary cross section view of a single well provided with countersunk edges.

FIG. 11 depicts the fragmentary cross section of a well 70 provided with countersunk edges 71.

The above embodiments are representative only and not intended to be limiting. Varying choices of materials, filters, fluorophores of varying intensities or fluorophores and the like are within the skill in the art and therefore included and contemplated in the scope of the invention.

What is claimed is:

1. A fluorescence validation microplate for testing the validity of a fluorescence microplate reader comprising a microplate having a plurality of wells therein, said plurality of wells comprising:
   (a) a first set of measurement wells in a 3×3 grid suitable for performing a cross-talk one-in-eight well design test wherein the center well of the first set contains a solid fluorophore and the outer wells of the first set contain no fluorophore;
   (b) a second set of measurement wells in a 3×3 grid suitable for performing a cross-talk eight-around-one well design test wherein the center of the second set contains no fluorophore and the outer wells of the second set each contains a solid fluorophore;
   (c) a third set of wells suitable for performing a linearity test wherein each well of the third set has a different concentration of solid fluorophore or the wells within the third set are decreasing in diameter;
   (d) a fourth set of wells suitable for performing an alignment test wherein each well of the fourth set has the same exact amount of solid fluorophore.

2. A microplate according to claim 1, wherein the microplate is constructed of a non-fluorescent, opaque material.

3. A microplate according to claim 1, wherein said third set of wells suitable for performing a linearity test consists of five sets of six wells of decreasing diameter.

4. A microplate according to claim 1, wherein said set of wells suitable for performing said alignment test consists of two rows of eight wells.

5. A microplate according to claim 1, wherein the solid fluorophore is selected from the group consisting of a fluorescent plastic, glass and paper material.

6. A microplate according to claim 1, which is a 96 well microplate.

7. A microplate according to claim 1, where the entrance of at least one of said wells is countersunk.

8. A microplate according to claim 1, which is a 384 or 1536 well microplate suitable for reading by a 384 or 1536 well fluorescence microplate readers, respectively.

9. A fluorescence validation microplate adapted for testing for cross-talk of a fluorescence microplate reader and fabricated from an opaque non-fluorescent material comprising a microplate having a plurality of wells therein, said plurality of wells comprising:
   (a) a first set of measurement wells in a 3×3 grid suitable for performing a cross-talk one-in-eight well design test wherein the center well of the first set contains a solid fluorophore and the outer wells of the first set contain no fluorophore;
   (b) a second set of measurement wells in a 3×3 grid suitable for performing a cross-talk eight-around-one well design test wherein the center of the second set contains no fluorophore and the outer wells of the second set each contains a solid fluorophore.

* * * * *